(12) United States Patent
Patel et al.

(10) Patent No.: US 8,980,794 B2
(45) Date of Patent: *Mar. 17, 2015

(54) AQUEOUS FORMULATIONS OF ASULAM

(75) Inventors: Smita Patel, Raleigh, NC (US); Mark D. Parrish, Raleigh, NC (US); Michael W. Edenfield, Bartow, FL (US); Atiur Rahman, Frankfurt (DE); Rainer Suessmann, Limburg (DE)

(73) Assignee: UPL Limited, Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,300

(22) Filed: Sep. 23, 2011
(Under 37 CFR 1.47)

(65) Prior Publication Data

US 2012/0021910 A1 Jan. 26, 2012

Related U.S. Application Data

(63) Continuation of application No. 11/401,511, filed on Apr. 11, 2006, now Pat. No. 8,399,379.

(51) Int. Cl.
*A01N 43/40* (2006.01)
*A01N 43/60* (2006.01)
*A01N 47/10* (2006.01)
*A01N 47/24* (2006.01)
*A01N 47/36* (2006.01)

(52) U.S. Cl.
CPC ..................... *A01N 47/36* (2013.01)
USPC ........... 504/130; 504/136; 504/215; 504/300; 504/302; 504/303

(58) Field of Classification Search
USPC .................. 504/136, 215, 305, 130
See application file for complete search history.

(56) References Cited

U.S. PATENT DOCUMENTS

| 6,093,680 | A | * | 7/2000 | Gillespie et al. | 504/363 |
| 8,399,379 | B2 | * | 3/2013 | Parrish | 504/130 |
| 2003/0060367 | A1 | * | 3/2003 | Bieringer et al. | 504/133 |

FOREIGN PATENT DOCUMENTS

WO  WO 2006/135497 A1  12/2006

OTHER PUBLICATIONS

RD 502007, Jan. 2006.*
International Preliminary Report on Patentability in PCT/US2006/016406, Dec. 11, 2007 (4 pages).
Written Opinion of the International Searching Authority in PCT/US2006/016406, Oct. 20, 2006 (3 pages).
Asulox XP Herbicide, Directions for Use (Specimen Label), Dec. 2006 (4 pages).
Jones et al., "Alternatives for Johnsongrass Control in Sugarcane", Proc. South. Weed Sci. Soc. 5:21 (2002).
Dalley et al., "Control of Rhizome Johnsongrass (*Sorghum halepense*) in Sugarcane with Trifloxysulfuron and Asulam", Weed Technology 22:397-401 (2008).

* cited by examiner

*Primary Examiner* — Alton Pryor
(74) *Attorney, Agent, or Firm* — Fish & Richardson P.C.

(57) ABSTRACT

This invention relates to a synergistic herbicidal composition comprising Component A comprised of i) 25 to 40% asulam, or its sodium salt; ii) 10 to 20% of a surfactant; iii) 0 to 1% of an antifoam; iv) 0 to 5% adjuvants and auxiliaries; and v) 40 to 65% water; and Component B comprised of trifloxysulfuron, or its herbicidally effective salts; wherein the ratio of Component A to Component B is in range of 80:1 to 380:1 based on active ingredient. The invention furthermore relates to a method of controlling weeds in crops of useful plants, especially in postemergence sugarcane, and to the use of this novel composition for this purpose.

21 Claims, No Drawings

AQUEOUS FORMULATIONS OF ASULAM

This application is a divisional application (and claims the benefit of priority under 35 USC 120) of U.S. application Ser. No. 11/401,511, filed Apr. 11, 2006, the entire contents of which are incorporated herein by reference in their entirety.

BACKGROUND OF THE INVENTION

This invention relates to a synergistic herbicidal combination comprising an aqueous formulation of asulam known as Asulox® XP and trifloxysulfuron. This invention also relates to a method of controlling the undesirable growth of difficult to control a broad spectrum of grass and broadleaf weeds when using this herbicidal combination.

SUMMARY OF THE INVENTION

This invention relates to a synergistic combination of Asulox® XP and trifloxysulfuron. The individual use of these herbicides has shown some success but in combination their synergistic effect has proven useful for the control of various weeds, especially broadleaf weeds, grasses and sedges in postemergence sugarcane. The invention furthermore relates to a method of controlling weeds in crops of useful plants, especially in postemergence sugarcane, and to the use of this novel composition for this purpose.

DETAILED DESCRIPTION OF THE INVENTION

The invention relates to the technical field of crop protection agents which can be used against unwanted vegetation and comprises, as active compounds, a combination of two herbicides. More specifically, it relates to a synergistic combination of a formulation of asulam known as Asulox® XP in combination with trifloxysulfuron.

According to another feature of the present invention, there is also provided a method for controlling the growth of weeds, i.e., undesired vegetation, at a locus which comprises applying to the locus a herbicidally effective amount of a mixture comprising Asulox® XP and trifloxysulfuron as defined herein. The mixture is applied as a post emergence application. The term "post-emergence application" refers to application to the aerial or exposed portions of the weeds which have emerged above the surface of the soil.

Asulam is commonly sold as the herbicide brand name Asulox® and is currently available in a special aqueous formulation providing greater efficacy as Asulox® XP. Asulox® XP is an aqueous crop protection formulation comprising asulam, an herbicidal thiocarbamate, known as methyl sullfanilylcarbamate, sodium salt.

Trifloxysulfuron is commonly sold as the herbicide brand name Envoke™. Envoke™ herbicide contains 75% by weight of trifloxysulfuron, also known as (2-pyridinesulfonamide, N-[[(4,6-dimethoxy-2-pyrimidinyl)-amino]carbonyl]-3-(222,trifluoroethoxy)-, monosodium salt, monohydrate.

Formulations of herbicidal active ingredients should generally have a high chemical and physical stability, good application qualities and user friendliness and a broad biological action combined with high selectivity. In general they are not employed in pure form. The herbicidal active ingredient asulam, which is generally employed as an aqueous solution under the trade name Asulox®, can have a disadvantage in that it has a high application rate in which it is applied to the areas to be treated.

By formulating an aqueous herbicidal composition comprising the herbicidal active ingredient asulam or its sodium salt, and at least one surfactant the goal can be achieved with Asulox® XP to provide an aqueous crop protectant formulation for the active ingredient asulam which has an improved herbicidal activity and at a lower application rate.

The surfactants can include any of the following: mixtures of quaternary ammonium compounds, sodium lauryl ether sulfate, fatty alcohol polyglycerol esters, and ethoxylated fatty amines.

An example of a mixture of quaternary ammonium compounds is Geronol® CF/AS30 (e.g., see Material Safety Data Sheet of Rhodia Asia Pacific Pte. Ltd., Singapore).

An example of a fatty alcohol polyglycerol ester is Synergen® B01, which constitutes a copolymer of glycerol, coconut fatty acid and phthalic anhydride and which is known under CAS no. 67746-02-5.

An example of an ethoxylated fatty amine (with 15 ethylene oxide units) is Rhodameen CF/15H® (e.g., see Material Safety Data Sheet of Rhodia Gerronnazzo S.P.A., Italy).

In addition, the aqueous formulation of asulam known as Asulox® XP can also additionally comprise antifoams (e.g., silicone based antifoams, preferably such as Rhodorsil® 481) and conventional adjuvants and additives such as antifreeze agents (e.g., from the group consisting of the ureas, diols and polyols, such as ethylene glycol and propylene glycol), colorants, fragrances and preservatives.

In a preferred embodiment for Asulox® XP, the aqueous herbicidal composition comprises the following by weight: a) 10 to 50% asulam; b) 1 to 30% of a surfactant from the surfactants listed above; c) 0 to 1% of an antifoam; d) 0 to 10% adjuvants and auxiliaries; e) 0 to 5% of a further herbicidal active ingredient; and f) 25 to 75% water. All percentages herein are by weight, unless otherwise noted.

In the most preferred embodiment for Asulox® XP, its composition comprises the following by weight: a) 25 to 40% asulam or its sodium salt; b) 10 to 20% of a surfactant as listed above; c) 0 to 1% of an antifoam; d) 0 to 5% of adjuvants and auxiliaries; e) 0 to 3% of a further herbicidal active ingredient; and f) 40 to 65% water.

The following are examples of the formulation for Asulox® XP:

Formulation Example No. 1:
  34.30 g of asulam (in the form of a sodium salt),
  13.57 g of Rhodapex® ES B70
  0.03 g of Rhodorsil® 481
  52.10 g of water
  The above ingredients are stirred to give a homogeneous solution.

Formulation Example No. 2:
  34.30 g of asulam (in the form of a sodium salt),
  13.97 g of Geronol® CF/AS30
  0.03 g of Rhodorsil® 481
  51.70 g of water
  The above ingredients are stirred to give a homogeneous solution.

Formulation Example No. 3:
  34.30 g of asulam (in the form of a sodium salt)
  13.57 g of Rhodameen CF/15H®
  0.03 g of Rhodorsil® 481
  52.10 g of water
  The above ingredients are stirred to give a homogeneous solution.

The surfactants and adjuvants used in this context mean:

| | |
|---|---|
| Geronol ® CF/AS30 | mixture of quaternary ammonium compounds, supplier: Rhodia |

| | |
|---|---|
| Rhodapex ® ESB 70/FEA | sodium lauryl ether sulfate (70% strength solution in water), supplier: Rhodia |
| Rhodorsil ® 481 | silicone-based antifoam, supplier: Rhodia |
| Rhodameen CF/15H ® | ethoxylated fatty amines, manufacturer: Rhone-Poulenc Geronazzo SpA, Div. of Rhone-Poulenc S.A |
| Synergen ® B01 | fatty alcohol polyglycerol ester (copolymer of glycerol, coconut fatty acid and phthalic anhydride), supplier: Clariant |

The abovementioned formulation auxiliaries of groups c) and d) in the preferred embodiments of Asulox XP are known to the skilled worker and are described, for example, in: Watkins, "Handbook of Insecticide Dust Diluents and Carriers", $2^{nd}$ Ed., Darland Books, Caldwell N.J., H.v. Olphen, "Introduction to Clay Colloid Chemistry"; $2^{nd}$ Ed., J. Wiley & Sons, N.Y.; C. Marsden, "Solvents Guide"; $2^{nd}$ Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active ethylene oxide adducts]", Wiss. Verlagsgesell., Stuttgart 1976; Winnacker-Küchler, "Chemische Technologie [Chemical technology]", Volume 7, C. Hauser Verlag Munich, 4th Ed. 1986.

The individual use of the herbicides Asulox® XP and trifloxysulfuron has shown some success but in combination their synergistic effect has proven useful for the control of various weeds, especially for post-emergence grass and broadleaf weed control in sugarcane. The combination of the herbicides increases the efficacy of grass and broadleaf weed control as compared to either product alone and the use of Asulox® XP instead of Asulox in combination with trifloxysulfuron allows a significant decrease in the amount of asulam needed to be applied for the same effectiveness.

Asulox® XP when combined with trifloxysulfuron acts synergistically to control weeds, especially for postemergence sugarcane weed control. The present invention furthermore also relates to a method for controlling undesired plant growth, preferably in crops of plants such as cereals (for example wheat, barley, rye, oats, rice, maize, sorghum and millet), sugar beet, oilseed rape, cotton, soybeans, and turf grass, and especially preferably in monocotyledonous crops such as cereals, for example wheat, barley, rye, oats, their hybridization products such as triticale, rice, maize, sorghum and millet, when the herbicidal compositions according to the invention are applied to the harmful plants, plant parts, plant seeds or the area on which the plants grow, for example the area under cultivation.

These herbicides are especially effective against broadleaf weeds such as redroot pigweed and prickly sida, as well as against grasses such as broadleaf signal grass, crabgrass, fall panicum and Johnsongrass.

The herbicide mixture according to the invention can be used against a large variety of weeds, such as broadleaf weeds, grasses, sedges and other agronomically important weeds. The herbicide mixture according to the invention is preferably suitable for controlling weeds in postemergence sugarcane.

The compositions according to the invention are suitable for all application methods conventionally used in agriculture for post-emergence applications.

The effectiveness of herbicides depends inter alia on the type of herbicide used, its application rate, the formulation, and the harmful plants to be controlled in each case, as well as climatic and soil conditions. A further criterion is the persistency or the rate at which the herbicide is degraded. Changes in the susceptibility of harmful plants to an active compound which may occur on prolonged use or in specific geographical areas may also have to be taken into account. Such changes manifest themselves by a more or less pronounced loss in activity and can only be compensated to a limited extent by higher herbicide application rates.

Owing to the large number of possible influencing factors, there is virtually no individual active compound which has all the desired properties for different requirements, in particular with respect to the species of harmful plants and the climatic zones. Furthermore, there is the permanent objective to achieve the desired effect using more and more reduced herbicide application rates. A lower application rate reduces not only the amount of active compound required for the application, but generally also reduces the amount of formulation auxiliaries required. Both reduce the economic expense and improve ecological compatibility of the herbicide treatment.

A frequently used method for improving the use profile of an herbicide is the combination of the active compound with one or more other active compounds which contribute the desired additional properties. However, when two or more active compounds are applied in combination, it is not uncommon for phenomena of physical and biological incompatibility to occur, for example insufficient stability of a joint formulation, decomposition of an active compound or antagonism of the active compounds. What is desired are, in contrast, active compound combinations having a favorable activity profile, high stability and, if possible, synergistically enhanced activity, thus permitting the application rate to be reduced, compared with the individual application of the active compounds to be combined.

Chemical mixtures can have an antagonistic effect when mixed, where the results are less than expected when the chemicals are combined. There can also be an additive effect, where the resultant mixture gives results expected from the sum of its components. Finally, there can be a synergistic effect where the results are greater than expected. A synergistic result is rare and typically only results from high concentrations. In the heavily regulated herbicide industry, high concentrations are not desirable in the environment. So when a synergistic effect is achieved at low doses, the resultant mixture is indeed a rare event.

A synergistic effect of herbicides is always present when the herbicidal activity of the active compound combinations exceeds the total of the activities of the active compounds when applied individually. The expected activity for a given combination of two active compounds can be calculated according to S. R. Colby ("Calculating Synergistic and Antagonistic Responses of Herbicide Combinations", Weeds 15, (1967), 20-22) as follows:

If

X is the percent inhibition of growth by herbicide A at an application rate of m g/ha, Y is the percent inhibition of growth by herbicide B at an application rate of n g/ha, and E is the expected growth as a percent of control with herbicides A+B when applying the active compounds A and B at application rates of m and n g/ha, Then $$E=100-(X+Y-XY/100).$$

The efficacy is calculated in %. 0% is an efficacy which corresponds to that of the control, while an efficacy of 100% means that no growth is observed.

If the actual herbicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The invention provides herbicidal compositions, comprising an effective amount of a mixture of Asulox XP and trifloxysulfuron.

The active compound combinations according to the invention can either be present as mixed formulations of the components A and B, if appropriate together with other customary formulation auxiliaries, which mixed formulations are then applied in the usual manner in the form of a dilution with water, or else they can be prepared in the form of so-called tank mixes by joint dilution with water of the components which are formulated separately, or partly separately or together in a co-formulation. Suitable general possibilities for formulations are, for example, wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed dressing products, granules for soil application or for broadcasting or water-dispersible granules (WG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4$^{th}$ Ed. 1986; van Valkenburg, "Pesticides Formulations", Marcel Dekker N.Y., 1973; K. Martens, "Spray Drying Handbook", 3$^{rd}$ Ed. 1979, G. Goodwin Ltd. London. The formulation auxiliaries required, such as inert materials, surfactants, solvents and other additives, are also known and are described, for example, in: Watkins, "Handbook of Insecticide Dust Diluents and Carriers", 2$^{nd}$ Ed., Darland Books, Caldwell N.J.; H. v. Olphen, "Introduction to Clay Colloid Chemistry"; 2$^{nd}$ Ed., J. Wiley & Sons, N.Y.; Marsden, "Solvents Guide", 2$^{nd}$ Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflachenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Vol. 7, C. Hauser Verlag Munich, 4th Ed. 1986.

The herbicide combinations according to the invention have a herbicidally active content of Asulox® XP and trifloxysulfuron and may comprise further components, for example other types of formulation auxiliaries and/or additives conventionally used in crop protection such as from the group of the safeners, and plant growth regulators, or they may be employed together with these.

The formulation auxiliaries required, such as inert materials, surfactants, solvents and other additives are also known and are described, for example, in Watkins, "Handbook of Insecticide Dust Diluents and Carriers", 2$^{nd}$ Ed., Dariand Books, Caldwell N.J.; H. V. Olphen, "Introduction to Clay Colloid Chemistry"; 2$^{nd}$ Ed., J. Wiley & Sons, N.Y. Marsden, "Solvents Guide", 2$^{nd}$ Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with safeners, fertilizers and/or growth regulators, may also be prepared, for example in the form of a readymix or a tank mix.

The publications cited contain detailed statements about preparation processes and starting materials. These publications are expressly incorporated into this description by way of reference.

EXAMPLES

| Component | Efficacy as Percent of Control | | | | |
|---|---|---|---|---|---|
| | Redroot Pigweed | Broadleaf SignalGrass | Crabgrass | Fall *Panicum* | Prickly Sida |
| A + NIS | 25 | 93 | 85 | 94 | 60 |
| B + NIS | 95 | 59 | 68 | 79 | 20 |
| TM | 100 | 99 | 99 | 99 | 78 |
| TM − E1 | 3.75 | 1.87 | 3.8 | 0.26 | 10 |

E1 = (B efficacy + A efficacy − ((B efficacy × A efficacy)/100)

where
Component A=Asulox® XP (4 pints/acre)
Component B=Envoke (0.3 oz/acre)
NIS=Nonionic surfactant as known to the skilled worker
TM=Tank mix (A+B+NIS)
E1=Expected efficacy if tank mix components are additive
TM-E1=Difference between expected additive effect and actual tank mix effect. Values greater than zero indicate synergy.

In the composition of the invention the weight ratio of trifloxysulfuron (as Envoke) is in the range of between 10 g active ingredient per hectare and 20 g active ingredient, per hectare, and preferably in the range of 14.5 g to 17.5 g active ingredient per hectare and asulam in the form of Asulox® XP is in a range from 1600 g active ingredient per hectare to 3740 g active ingredient per hectare, preferably in the range of 1600 g to 1800 g active ingredient per hectare.

Although the invention has been described with reference to preferred embodiments and examples thereof, the scope of the present invention is not limited only to those described embodiments. As will be apparent to those skilled in the art, adaptations and modifications to the invention described above can be made without departing from the spirit and scope of the invention, which is defined by the following claims.

What is claimed is:

1. An herbicidal composition comprising:
   i) 25 to 40% asulam, or its sodium salt, as active ingredient;
   ii) 10 to 20% of sodium lauryl ether sulfate or ethoxylated fatty amine or a mixture thereof;
   iii) a silicone-based antifoam present up to 1%;
   iv) 0 to 5% adjuvants and auxiliaries; and
   v) 40 to 65% water.

2. The herbicidal composition of claim 1 wherein the composition comprises 10 to 20% sodium lauryl ether sulfate.

3. The herbicidal composition of claim 1 wherein the composition comprises 10 to 20% ethoxylated fatty amine.

4. The herbicidal composition of claim 1, wherein the composition comprises 0.03 g of a silicone based anti-foam.

5. The composition of claim 1, further comprising trifloxysulfuron, or its herbicidally effective salt.

6. A method for controlling unwanted vegetation in cereal crops at a locus comprising applying postemergently to said locus an effective amount of an herbicidal composition comprising:
 i) 25 to 40% asulam, or its sodium salt, as active ingredient;
 ii) 10 to 20% of sodium lauryl ether sulfate or ethoxylated fatty amine or a mixture thereof;
 iii) a silicone-based antifoam present up to 1%;
 iv) 0 to 5% adjuvants and auxiliaries; and
 v) 40 to 65% water.

7. The method of claim 6 wherein the herbicidal composition comprises from between 1600 g of the active ingredient per hectare and 3740 g of the active ingredient per hectare.

8. The method of claim 6 wherein the unwanted vegetation is chosen from group consisting of broadleaf weeds, grasses and sedges.

9. The method of claim 6 wherein the herbicidal composition comprises 1750 g of the active ingredient per hectare.

10. The method of claim 6, wherein the composition comprises 0.03 g of a silicone based anti-foam.

11. A method for controlling unwanted vegetation in sugarcane at a locus comprising applying postemergently to said locus an effective amount of an herbicidal composition comprising:
 i) 25 to 40% asulam, or its sodium salt, as active ingredient;
 ii) 10 to 20% of sodium lauryl ether sulfate or ethoxylated fatty amine or a mixture thereof;
 iii) a silicone-based antifoam present up to 1%;
 iv) 0 to 5% adjuvants and auxiliaries; and
 v) 40 to 65% water.

12. The method of claim 11 wherein the herbicidal composition comprises from between 1600 g of the active ingredient per hectare and 3740 g of the active ingredient per hectare.

13. The method of claim 11 wherein the unwanted vegetation is chosen from group consisting of broad leaf weeds, grasses and sedges.

14. The method of claim 11 wherein the herbicidal composition comprises 1750 g of the active ingredient per hectare.

15. The method of claim 11, wherein the composition comprises 0.03 g of a silicone based anti-foam.

16. A method for controlling unwanted vegetation in sugar beet, oilseed rape, cotton, soybeans and turf grass at a locus comprising applying postemergently to said locus an effective amount of an herbicidal composition comprising:
 i) 25 to 40% asulam, or its sodium salt, as active ingredient;
 ii) 10 to 20% of sodium lauryl ether sulfate or ethoxylated fatty amine or a mixture thereof;
 iii) a silicone-based antifoam present up to 1%;
 iv) 0 to 5% adjuvants and auxiliaries; and
 v) 40 to 65% water.

17. The method of claim 16 wherein the herbicidal composition comprises from between 1600 g of the active ingredient per hectare and 3740 g of the active ingredient per hectare.

18. The method of claim 16 wherein the unwanted vegetation is chosen from group consisting of broadleaf weeds, grasses and sedges.

19. The method of claim 16 wherein the herbicidal composition comprises 1750 g of the active ingredient per hectare.

20. The method of claim 16, wherein the composition comprises 0.03 g of a silicone based anti-foam.

21. An herbicidal composition consisting essentially of:
 i) 34.30 g of asulam sodium as active ingredient;
 ii) 13.57 g of sodium lauryl ether sulfate or 13.57 g of an ethoxylated fatty amine;
 iii) 0.03 g of a silicone based anti-foam; and
 iv) 52.1 g water.

\* \* \* \* \*